United States Patent
Wilson et al.

(10) Patent No.: US 12,259,504 B2
(45) Date of Patent: Mar. 25, 2025

(54) MODULAR X-RAY DETECTORS AND SYSTEMS

(71) Applicant: Varex Imaging Corporation, Salt Lake City, UT (US)

(72) Inventors: Tyler Wilson, Stansbury Park, UT (US); Maxwell J. Allen, Redwood City, CA (US); Steven Freestone, Sandy, UT (US); Carlo Tognina, Salt Lake City, UT (US); Paul Pryor, West Jordan, UT (US); Christy Patterson, West Jordan, UT (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 0 days.

(21) Appl. No.: 17/922,348

(22) PCT Filed: Sep. 29, 2022

(86) PCT No.: PCT/US2022/045282
§ 371 (c)(1),
(2) Date: Oct. 28, 2022

(87) PCT Pub. No.: WO2023/055970
PCT Pub. Date: Apr. 6, 2023

(65) Prior Publication Data
US 2024/0255655 A1   Aug. 1, 2024

Related U.S. Application Data

(60) Provisional application No. 63/250,198, filed on Sep. 29, 2021.

(51) Int. Cl.
*G01T 1/17* (2006.01)

(52) U.S. Cl.
CPC ................. *G01T 1/17* (2013.01)

(58) Field of Classification Search
CPC ........................................... G01T 1/17
See application file for complete search history.

(56) References Cited

U.S. PATENT DOCUMENTS

2010/0301223 A1   12/2010   Kobayashi
2011/0254563 A1   10/2011   Liu et al.
(Continued)

FOREIGN PATENT DOCUMENTS

JP   2012143334 A   1/2015

OTHER PUBLICATIONS

Int'l Appl. No. PCT/US2022/045282, International Search Report dated Jan. 20, 2023.
(Continued)

*Primary Examiner* — Kiho Kim
(74) *Attorney, Agent, or Firm* — Dorsey & Whitney LLP

(57) ABSTRACT

Some embodiments include an x-ray detector, comprising a housing; a sensor array disposed in the housing and configured to generate image data in response to incident x-rays; a control logic disposed in the housing; a connector interface integrated with the housing; and an adapter removably couplable to the connector interface; wherein: the control logic is configurable to operate in a plurality of operating modes; and for a first operating mode of the operating modes, the control logic is configured to process the image data and/or transmit the image data through the adapter differently than for a second operating mode of the operating modes.

19 Claims, 8 Drawing Sheets

(56) References Cited

U.S. PATENT DOCUMENTS

| | | | |
|---|---|---|---|
| 2012/0281817 A1 | 11/2012 | McBroom et al. | |
| 2014/0226795 A1* | 8/2014 | Kitano | A61B 6/56 378/189 |
| 2015/0071414 A1* | 3/2015 | Oda | A61B 6/548 378/207 |
| 2017/0373115 A1 | 12/2017 | Menichelli et al. | |

OTHER PUBLICATIONS

Int'l Appl. No. PCT/US2022/045282, Written Opinion dated Jan. 20, 2023.

* cited by examiner

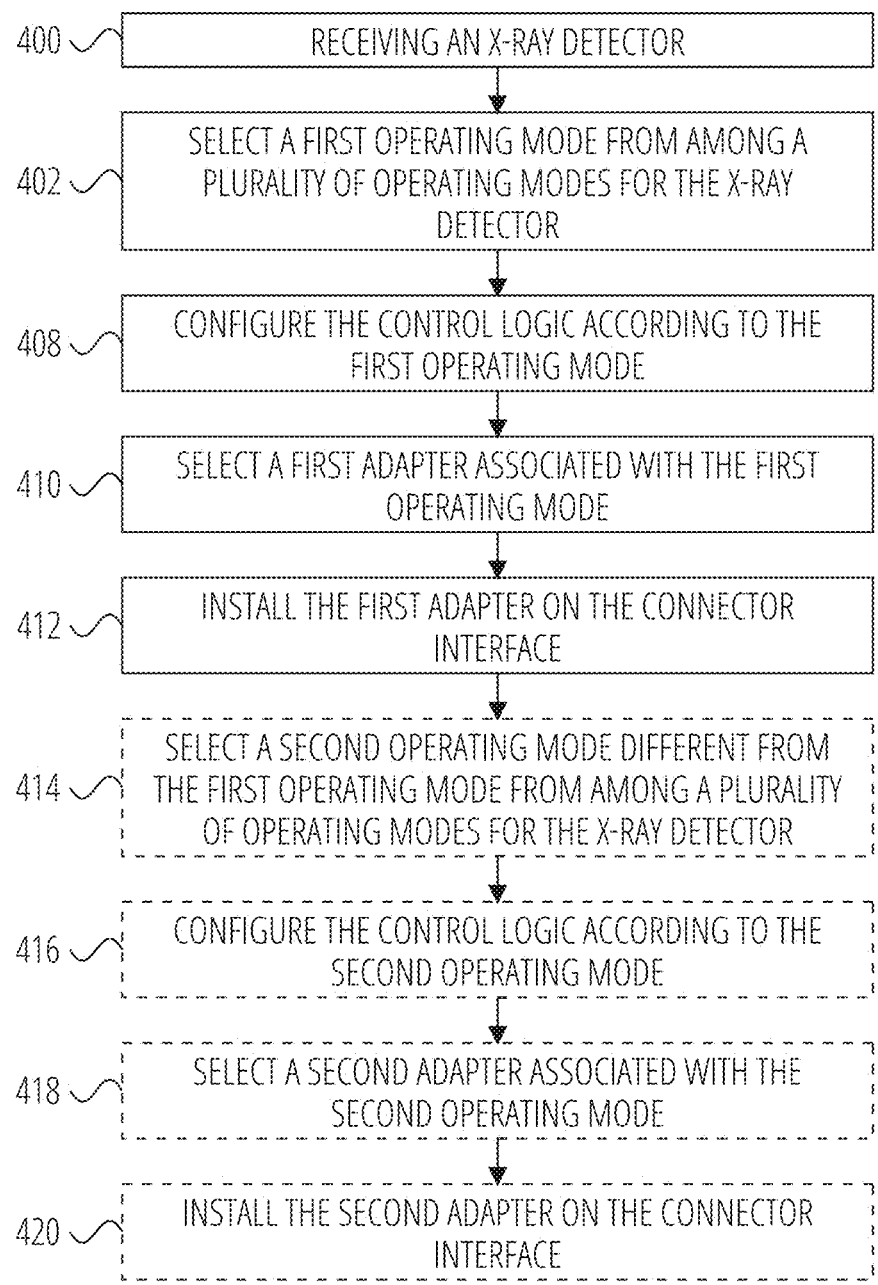

MODULAR X-RAY DETECTORS AND SYSTEMS

CROSS-REFERENCE TO RELATED APPLICATIONS

This application is a national stage entry under 35 U.S.C. 371 of PCT Application No. PCT/US2022/045282, filed 29 Sep. 2022, and claims priority to U.S. Application No. 63/250,198, filed 29 Sep. 2021, the disclosures of which are incorporated herein by reference in their entireties.

X-ray detectors may be used to generate two-dimensional images or video in response to incident x-rays. The x-ray detectors may be designed according to a specific specification, such as a customer's specification. Different designs, such as different customers, may have different specifications. As a result, the same x-ray detector may need to be redesigned to operate in different systems, such as systems of different customers.

BRIEF DESCRIPTION OF SEVERAL VIEWS OF THE DRAWINGS

FIG. 4 is a flowchart of configuring an x-ray detector according to some embodiments.

DETAILED DESCRIPTION

Some embodiments relate to modular x-ray detectors and systems and in particular, modular x-ray detectors and systems with adapters. X-ray detectors may be used in a variety of applications. Some systems, such as a cone beam computed tomography (CBCT) system may use a high reliability communication technique to ensure that each image arrives at a host computer. Other types of systems, such as surgical intervention systems, use a low latency communication technique to minimize a delay or guarantee a maximum delay between image acquisition and image display to improve hand/eye coordination of a surgeon.

Certain hardware interfaces may support a system behavior such as high reliability communication while other hardware interfaces support low latency communication. If an x-ray device is configured with hardware that supports one mode of operation it may not be capable of supporting the other operation or different operations. As a result, different types x-ray detectors may be needed to support both or multiple operations. Multiple types x-ray detectors may increase costs for a consumer, increase costs for manufacturers, and increase costs for maintenance. Embodiments described herein allow a single modular x-ray detector with adapters to support multiple modes of operation that would otherwise require multiple different x-ray detectors.

Figure 1:
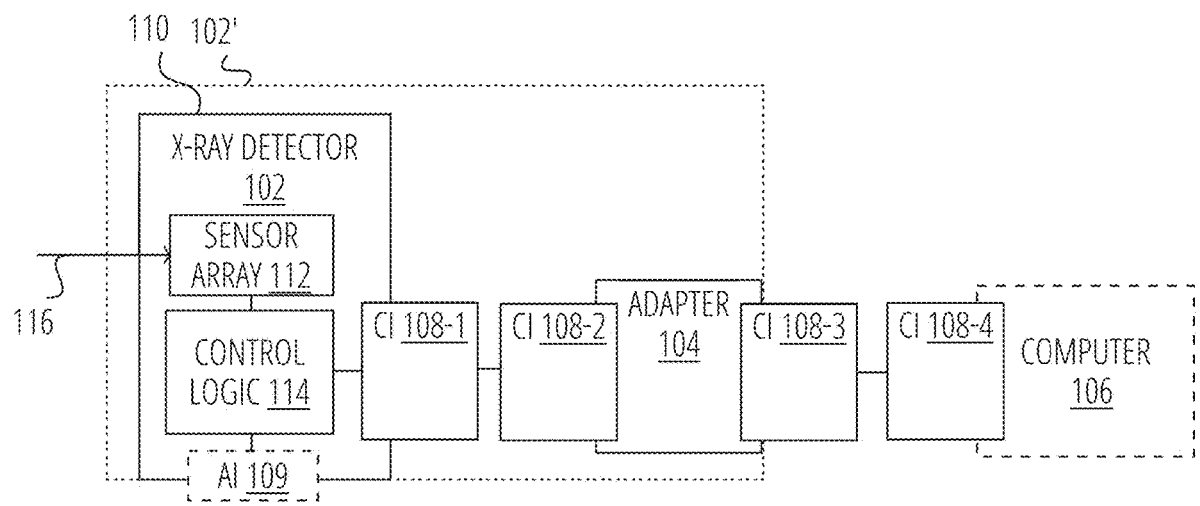
FIG. 1 is a block diagram an x-ray detector with an adapter according to some embodiments.

FIG. 1 is a block diagram of an x-ray detector including an adapter according to some embodiments. Some embodiments include a modular x-ray detector 102'. The modular x-ray detector 102' includes an x-ray detector 102 and an adapter 104. The x-ray detector 102 and the adapter 104 are integrated together to form the modular x-ray detector 102'.

The x-ray detector 102 is a device configured to acquire data in response to incident x-rays 116. In some embodiments, the data may include image data, video data, or the like. The x-ray detector 102 includes a housing 110, a sensor array 112, a control logic 114, and a first connector interface 108-1. The housing 110 is configured to encapsulate the sensor array 112 and the control logic 114.

The sensor array 112 is configured to generate an image in response to incident x-ray radiation 116 and disposed in the housing. The sensor array 112 may include a variety of sensors configured to generate data based on incident x-rays. The sensor array 112 may include direct conversion sensors, indirect conversion sensors and x-ray conversion materials (e.g., scintillator materials), or the like.

The control logic 114 is disposed in the housing 110 and coupled to the sensor array 112. The control logic 114 is configured to control the sensor array 112, processing of image data from the sensor array 112, transmission of that data from the x-ray detector 102, and other operations of the x-ray detector 102. The control logic 114 may include a general purpose processor, a digital signal processor (DSP), an application specific integrated circuit (ASIC), a microcontrol logic, a programmable logic device (e.g., field-programmable gate array (FPGA)), discrete circuits, a combination of such devices, or the like. In addition, other interface devices, such as circuit chipsets, hubs, memory control logics, communication interfaces, or the like may be part of the control logic 114 to connect the control logic 114 to internal and external components of the x-ray detector 102.

The first connector interface 108-1 is integrated at least partially on an exterior of the housing 110. The first connector interface 108-1 is electrically connected to the control logic 114.

The adapter 104 is a device that is removably couplable to the x-ray detector 102 at the first connector interface 108-1. The adapter 104 includes at least two connector interfaces. Here, the adapter 104 includes a second connector interface 108-2 and a third connector interface 108-3. The second connector interface 108-2 is configured to physically and electrically mate with the first connector interface 108-1. For example, the first connector interface 108-1 and the second connector interface 108-2 may be configured according to a specification of a standardized connector interface such as small form-factor pluggable (SFP) interface, SFP+, quad small form-factor pluggable (QSFP), QSFP+, QSFP28, XFP, C form-factor pluggable (CFP), Universal Serial Bus (USB), Ethernet, fiber optic, or the like. However, in other embodiments, the first connector interface 108-1 and the second connector interface 108-2 may be proprietary connector interfaces.

The third connector interface 108-3 may be the same or different from the first and second connector interfaces 108-1 and 108-2. For example, third connector interface 108-3 may include an RJ-45 interface, a fiber optic interface, an Ethernet interface, an Energy Efficient Ethernet (EEE)

interface, a Synchronous Optical Networking (SONET) interface, an SDH interface, a Plesiochronous Digital Hierarchy (PDH) interface, a FieldBus interface, a token ring interface, an optical transport network (OTN) interface, a single mode fiber (SMF) interface, a multimode fiber interface (MMF), or the like.

The control logic 114 is configurable to operate in multiple operating modes. Operating modes are the method or means of operation for the system and are characterized by the hardware and desired use of the detector as a high performance detector, a high reliability detector, or other applications as required by the system. In different operating modes, the control logic 114 may process and/or transmit data from the sensor array 112 differently. For example, in one operating mode, the control logic 114 may be configured to transmit image data from the sensory array 112 with a higher reliability or a guaranteed reliability while in another operating mode the control logic 114 may be configured to transmit the image data with a lower latency. In the multiple operating modes, the processing of image data and/or the transmission of the image data through the adapter 104 is different for a first one of the operating modes than another of the operating modes. The control logic 114 may be currently configured to operate in a first operating mode and not in a second operating mode. However, the control logic 114 may be reconfigured to operate in the second operating mode. In other embodiments, the control logic 114 may be configured to operate in either mode depending on the adapter 104.

The control logic 114 and the connector interface 108-1 are configured to transmit data at a data rate greater than or equal to a greatest data rate among the operating modes. Even if the current adapter 104 is not capable of such transmission at the greatest data rate, the control logic 114 and the connector interface 108-1 are configured to transmit at that rate as another operating mode associated with a different adapter 104 may operate at a higher data rate.

The different adapters 104 and different operating modes use the same x-ray detector 102. However, the modular x-ray detector 102' has the different operating mode. A single x-ray detector 102 may be tracked as a single part number, tested using a single test procedure and a single set of test equipment, or the like. The x-ray detector 102 may be replaced by an identical x-ray detector 102 regardless of the adapter 104 or operating mode.

While the different adapters 104 may need to be tracked and tested separately, more complex and/or expensive components such as the sensor array 112 may not need to be tested multiple times for multiple different operating modes. The interface provided by the adapter 104 may have no effect on testing of the sensor array 112. If the adapter 104 fails, the x-ray detector 102 may be used with another adapter 104 without a need to retest the x-ray detector 102. Moreover, there is no need to retest the x-ray detector 102 if the adapter 104 is changed.

In some embodiments, the modular x-ray detector 102' may be coupled to a computer 106. The computer 106 may include a system in which the modular x-ray detector 102' may be installed, an original equipment manufacturer (OEM) system that is configuring the modular x-ray detector, a technician or other user's computer, or the like. The computer 106 may be configured to store multiple sets of configuration data for multiple operating modes. Each of the operating modes may be associated with a different set of configuration data. Each of the sets of configuration data may include firmware, software, or the like for the control logic 114. In addition, the configuration data may include configuration data for the adapter 104. When the control logic 114 is configured with a particular set of configuration data, the control logic 114 is configured to operate in the associated operating mode. The configuration data includes information used to setup the control logic 114 to perform the function of any given operation. For example, one set of configuration data may include software and firmware for the control logic 114 that, when executed by the control logic 114 causes the control logic 114 to operate in a higher reliability or guaranteed reliability operating mode. For a different set of configuration data, the set of configuration data may include software and firmware for the control logic 114 that, when executed by the control logic 114 causes the control logic 114 to operate in a lower latency operating mode.

In some embodiments, the control logic 114 may be configured to communicate with the computer 106 to receive a set of configuration data associated with a currently installed adapter 104. The control logic 114 may be configured to identify itself and the adapter 104 to the computer 106 so that the computer 106 may transmit the associated set of configuration data. In other embodiments, the computer 106 may transmit a set of configuration data based on an identification of the adapter 104 and/or a selected operating mode for the modular x-ray detector 102'.

Although the configuration data may be transmitted to the control logic 114 through the adapter 104, in other embodiments, the configuration data may be transmitted in different ways. For example, the x-ray detector 102 may include an alternate interface (AI) 109 such as a wireless communication interface such as WiFi, Bluetooth, or the like. The set of configuration data may be transmitted through the wireless communication interface. In other embodiments, the alternate interface 109 may include an alternate physical interface such as USB, External SATA (eSATA), Firewire, a memory card slot, or the like. The computer 106 and/or a computer readable medium including the set of configuration data may be attached to the alternate physical interface and transmitted to the control logic 114.

The different adapter 104 and the different associated set of configuration data may transform the modular x-ray detector 102' into a different device. For example, one set of a first adapter 104 and a first set of configuration data may configure the modular x-ray detector 102' to operate with high reliability. For example, the first set of configuration data may implement a communication protocol such as the Transmission Control Protocol (TCP) or another protocol that may guarantee transmission of all data in order over a potentially unreliable network. Additional buffering, feedback to prevent lost images, or the like may be performed by the control logic 114 to ensure that data is not lost even if the acquisition of the data from the modular x-ray detector 102' is relatively delayed. In a particular example, the high reliability mode of operation may be used with a computed tomography (CT) system where multiple images and multiple exposures are performed during a single scan of a patient. If one of the images is corrupted or lost, the entire procedure may need to be performed again, increasing a dose received by the patient.

A second adapter 104 and an associated second set of configuration data may configure the modular x-ray detector 102' to operate using a lower latency protocol such as User Datagram Protocol (UDP), CoaXPress, a streaming video protocol, or the like. Accordingly, the same x-ray detector 102 may be used with different adapters 104 and/or different sets of configuration data to operate as a high reliability device or a low latency device. In a particular example, a modular x-ray detector 102' configured to low latency may be used in an interventional procedure where a surgeon is watching a real-time image while performing a procedure, such as installing a stent. Delays in the processing between the acquisition of an image and the transmission of the image from the modular x-ray detector 102' may be minimized by the set of configuration data and the particular adapter 104. Although high reliability and low latency have been used as examples of characteristics of different combinations of sets of configuration data and adapters 104, in other embodiments, different combinations may have different characteristics.

In some embodiments, the modularity and reconfigurability of the x-ray detector 102 allows for additional configurations as new adapters 104 become available. For example, a new adapter 104 with an SFP+ form factor may be developed. That new adapter 104 may be installed on an existing x-ray detector 102 and a new set of configuration data may be installed on the control logic 114. As a result, new operating modes may be available with the same x-ray detector 102. In some embodiments, the new operating modes may become available without returning the modular x-ray detector 102' to an OEM.

By using an x-ray detector 102 as part of a modular x-ray detector 102', a manufacturer may reduce costs, delays, maintenance burdens, or the like. The manufacturer may design and support a single x-ray detector 102 that may be integrated with different adapters 104 and different sets of configuration data to provide different and possibly mutually exclusive modes of operation. Moreover, a user's costs may be reduced. An end user may no longer need to purchase separately configured x-ray detectors for two or more different applications. A single x-ray detector 102 may be reconfigured as described herein and used for a different application.

Figure 2:
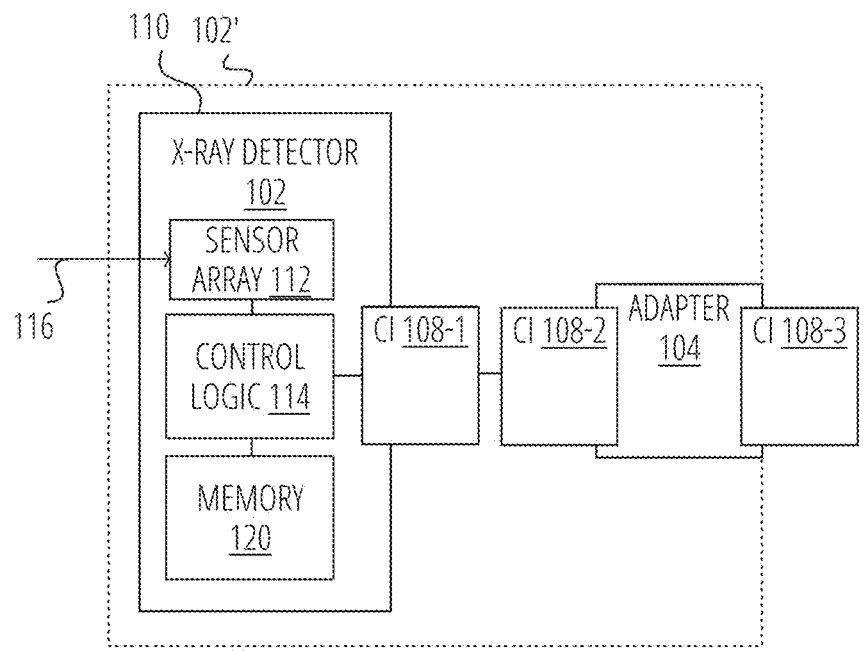
FIG. 2 is a block diagram an x-ray detector with a memory configured to store a plurality of sets of configuration data according to some embodiments.

FIG. 2 is a block diagram an x-ray detector with a memory configured to store a plurality of sets of configuration data according to some embodiments. The modular x-ray detector 102' may be similar to the modular x-ray detector 102' of FIG. 1 described above. However, the x-ray detector 102 includes a memory 120.

The memory 120 may include a dynamic random access memory (DRAM) module, according to various standards such as DDR-DDR5, static random access memory (SRAM), non-volatile memory such as Flash, spin-transfer torque magentoresistive random access memory (STT-MRAM), or Phase-Change RAM, magnetic or optical media, or the like. The memory 120 may include combinations of such storage devices.

The memory 120 may be configured to store multiple sets of configuration data. Each of the operating modes may be associated with a different set of configuration data. Each of the sets of configuration data may include firmware, software, or the like for the control logic 114. In addition, the configuration data may include configuration data for the adapter 104.

The memory 120 may store an indication of a current operating mode for the modular x-ray detector 102'. The current operating mode may include a flag, a register, a storage location of the memory 120, or the like with information that indicates the current operating mode. Based on the indication of the current operating mode, the control logic 114 may be configured to select a set of configuration data. The control logic 114 may be configured to operate in the current operating modes using the selected set of configuration data.

In some embodiments, the control logic 114 is configured to select one of the operating modes based on the adapter 104. For example, the control logic 114 may be configured to communicate with the adapter 104 such as through an Inter-Integrated Circuit (I2C) interface of the connector interfaces 108-1 and 108-2. Through the I2C interface, the control logic 114 may receive an indication of the adapter 104, an indication of an operating mode stored on the adapter 104 similar to the indication of the current operating mode described above, or the like. Based on that information, the control logic 114 may select one of the operating modes. In some embodiments, the information received may be an indication of the operating mode itself. In other embodiments, the control logic 114 may transform the information into an indication of an operating mode. For example, the control logic 114 may identify the adapter 104. That adapter 104 may be associated with a single operating mode. That single operating mode may be selected and use to select the associated set of configuration data. The control logic 114 may be configured to operate in the selected one of the operating modes using the associated set of configuration data.

Figure 3A:
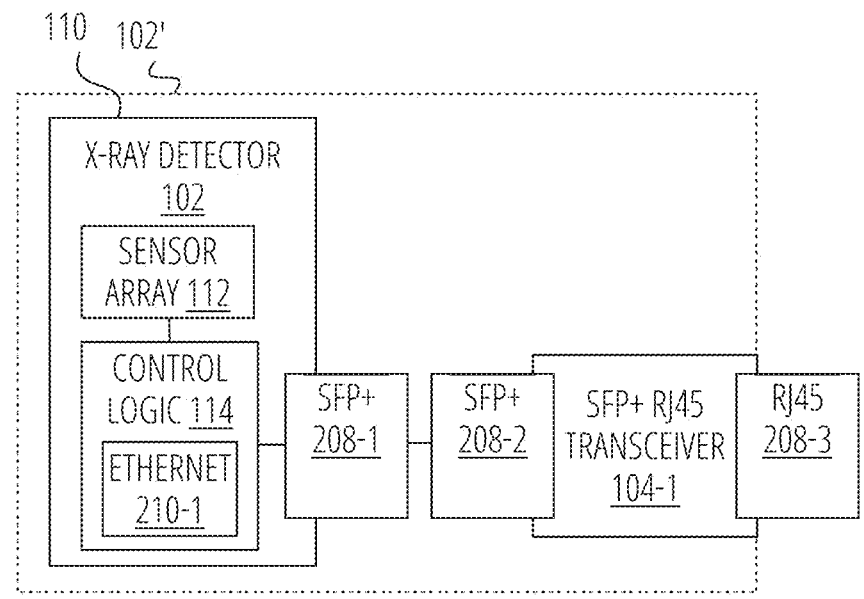
FIGS. 3A-3B are block diagrams of an x-ray detector with different adapters according to some embodiments.
Figure 3B:
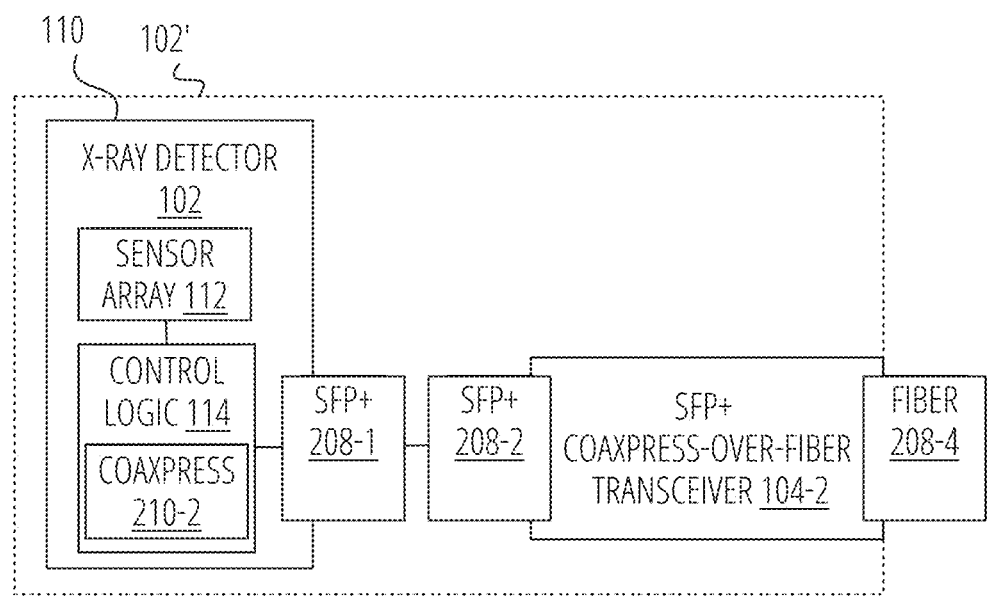

FIGS. 3A-3B are block diagrams of an x-ray detector with different adapters according to some embodiments. Referring to FIG. 3A, the modular x-ray detector 102' may be similar to the modular x-ray detectors 102' described above. However, the first connector interface 108-1 is an SFP+ interface 208-1. The adapter 104 is an SFP+ to RJ45 transceiver 104-1. The third connection interface 108-3 is an RJ45 interface 208-3. The control logic 114 is configured to communicate through an RJ45 interface, such as by using TCP over Ethernet as represented by the Ethernet 210-1 configuration.

Referring to FIG. 3B, the modular x-ray detector 102' is identical to the modular x-ray detector 102' of FIG. 3A except for the adapter 104 and the configuration of the control logic 114. In particular, the x-ray detector 102 hardware is the same. The adapter 104 is an SFP+ to CoaXPress-over-Fiber transceiver 104-2. The third connection interface 108-3 is a fiber interface 208-4. The control logic 114 may be configured to communicate over the fiber interface 208-4 according to the CoaXPress standard as represented by the CoaXPress 210-2 configuration.

Accordingly, the x-ray detector 102 may be configured or reconfigured to operate in at least two operating modes. The first operating mode is TCP over Ethernet and the second operating mode is CoaXPress over fiber. As a result, the first operating mode may have a latency higher than that of the second operating mode while the first operating mode has a reliability higher than the second operating mode.

FIG. 4 is a flowchart of configuring an x-ray detector according to some embodiments. Referring to FIGS. 1, 2 and 4, the modular x-ray detector 102' will be used as an example. In 400, an x-ray detector 102 is received.

In 402, a first operating mode is selected from among a plurality of operating modes for the x-ray detector. For example, an indication of an operating mode may be set in the control logic 114. In another example, an operating mode may be selected on the computer 106.

In 408, the control logic 114 is configured according to the first operating mode. For example, software, firmware, or the like may be loaded on the control logic 114 through the alternate interface 109. In another example, a set of configuration data may be selected from a memory 120 and loaded on the control logic 114.

In 410, a first adapter 104 associated with the first operating mode is selected. The first adapter 104 may be associated with other operating modes, however the set of configuration data and the adapter 104 create a specific combination. In 412, the first adapter 104 is installed on the connector interface 108-1.

While operations 408, 410, and 412 have been described in a particular order, in other embodiments, the order may be different. For example, the adapter may be selected in 410 and installed in 412 before configuring the control logic 114 in 408. The configuring of the control logic in 408 may be performed through communication through the installed first adapter 104.

For example, the computer 106 may select an operating mode. The first operating mode may be input to the computer 106. In other embodiments, the memory 120 may include an indication of the first operating mode. The first operating mode may be communicated to the computer 106. The computer 106 may store set of configuration data for multiple operating modes for the modular x-ray detector 102'. The computer 106 may select the set of configuration data for the first operating mode. The selected set of configuration data may be transmitted to the control logic 114 and used to configure the control logic in 408.

In some embodiments, the modular x-ray detector 102' may be reconfigured for a second operating mode. In 414, a second operating mode different from the first operating mode is selected from among the operating modes for the x-ray detector after configuring the control logic 114 according to the first operating mode in 408. The second operating mode may be selected similarly to selecting the first operating mode in 402. In 416, the control logic 114 is configured according to the second operating mode. The control logic 416 may be configured in a manner similar to the configuration in 408 but with the configuration data associated with the second operating mode.

In some embodiments, after selecting a second operating mode in 414, the adapter 104 may remain the same. The set of configuration data used to configure the control logic 114 according to the second operating mode in 416 may be different from that of the first operating mode but associated with the same first adapter 104. In other embodiments, the second operating mode may be associated with a second adapter 104 different from the first adapter 104. In 418, a second adapter different from the first adapter 104 associated with the second operating mode is selected. In 420, the second adapter 104 is installed on the connector interface 108-1.

In some embodiments, the change of an adapter 104 may trigger the reconfiguration of the control logic 114. For example, a second operating mode is selected in 414. Then, in 418 a second adapter is selected and installed in 420. The control logic 114 may be configured to detect the second adapter 104 and determine the second operating mode and the associated set of configuration data based on the second adapter 104 as described above. The control logic 114 may then reconfigure itself according to the second operating mode. As a result, the mere changing of an adapter 104 from one type to another may convert the modular x-ray detector 102' into a different device.

Figure 5:
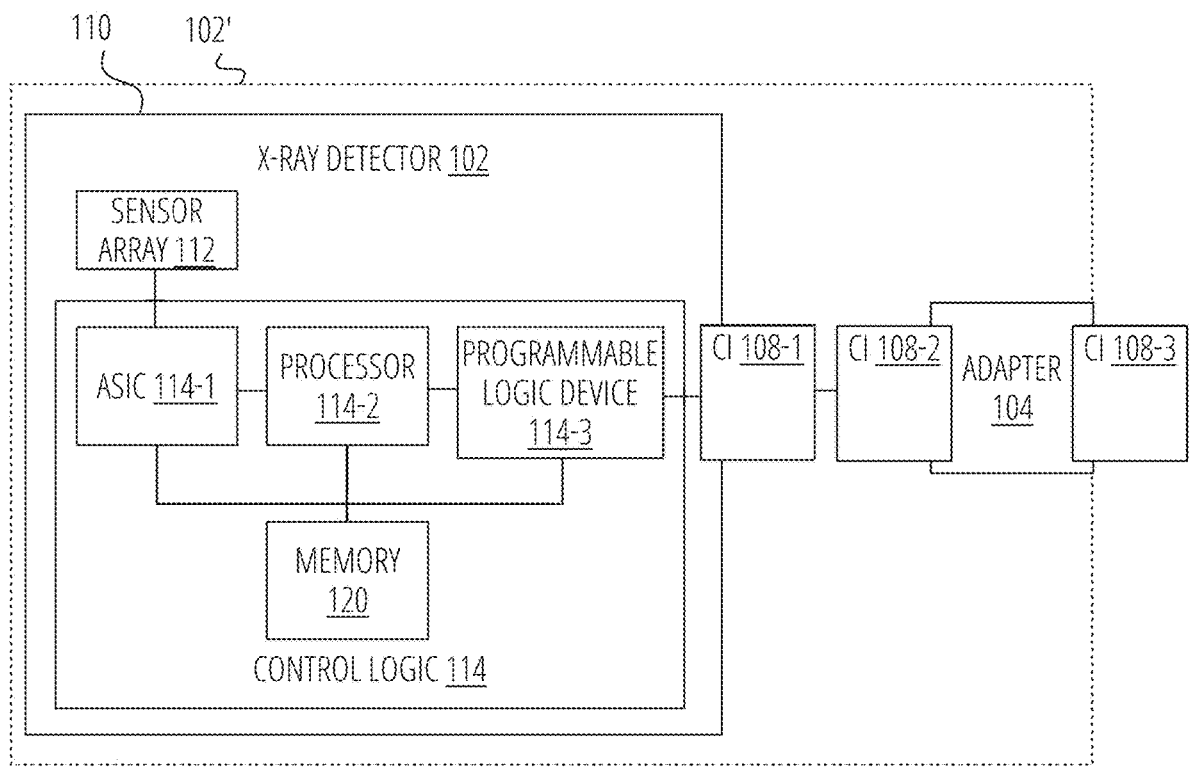
FIG. 5 is a block diagram of an x-ray detector with processors and/or programmable logic devices according to some embodiments.

FIG. 5 is a block diagram of an x-ray detector with processors and/or programmable logic devices according to some embodiments. The modular x-ray detector 102' may be similar to the modular x-ray detectors 102' described above. In some embodiments, the control logic 114 includes an application specific integrated circuit (ASIC) 114-1, a processor 114-2, and a programmable logic device 114-3. The ASIC 114-1, a processor 114-2, and a programmable logic device 114-3 are coupled to the memory 120.

The ASIC 114-1 is an application specific integrated circuit configured to read out image data from the sensor array 112. The ASIC 114-1 may store the image data in the memory. The processor 114-2 may include a central processing unit (CPU) such as an advanced RISC machines (ARM) processor, a reduced instruction set computer (RISC) processor, an x64 processor, or the like. Example of the programmable logic device 114-3 include a field programmable gate array (FPGA), a complex programmable logic devices (CPLD), programmable array logic (PAL), or the like.

The processor 114-2 and the programmable logic device 114-3 may share the memory 120. The memory 120 may be apportioned according to the operating mode. As described above, when the control logic 114 is configured according to the operating mode, part of that configuration may include apportioning the memory between the processor 114-2 and programmable logic device 114-3. Some portions of the memory 120 may be shared between the processor 114-2 and programmable logic device 114-3.

In some embodiments, configuring the control logic 114 may include changing software of a processor 114-2 of the control logic 114 based on the operating mode. In particular, the software that is changed may include the portion associated with transmission of data through the adapter 104. Similarly, configuring the control logic 114 may include changing a configuration of a programmable logic device 114-3 of the control logic 114 based on the operating mode. For example, various cores, blocks, connections, or the like of the programmable logic device 114-3 may be changed based on the operating mode. The change in the configuration may include a change associated with transmission of data through the adapter 104.

In some embodiments, the reconfiguration of the control logic 114 may include changes to software, firmware, or other configurations of both the processor 114-2 and programmable logic device 114-3. However, in other embodiments, software, firmware, or other configurations related to only one of the processor 114-2 and the programmable logic device 114-3 may be changed when changing to a new operating mode.

Figure 6:
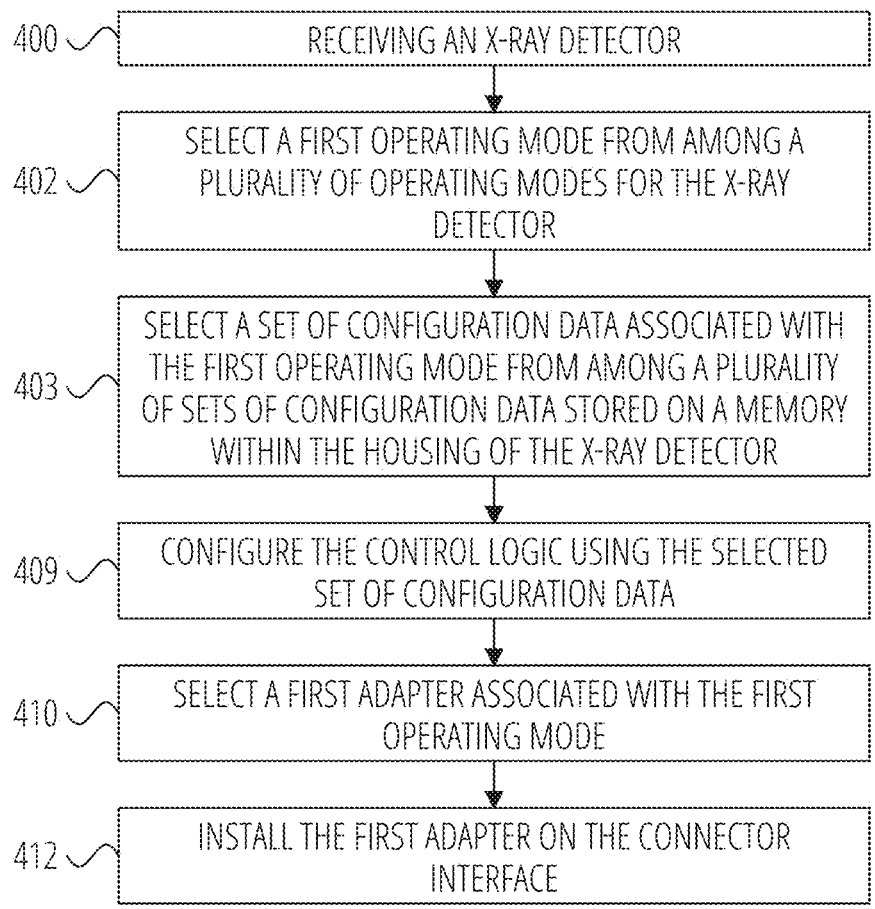
FIG. 6 is a flowchart of configuring an x-ray detector with a memory configured to store a plurality of sets of configuration data according to some embodiments.

FIG. 6 is a flowchart of configuring an x-ray detector with a memory configured to store a plurality of sets of configuration data according to some embodiments. Referring to FIGS. 2 and 6, in some embodiments, the operation may be similar to that of FIG. 4. However, in 403, a set of configuration data associated with the first operating mode is selected from among a plurality of sets of configuration data stored on a memory 120 within the housing 110 of the x-ray detector 102. In 409, the control logic 114 is configured using the selected set of configuration data. Accordingly, the modular x-ray detector 102' may be preconfigured with multiple sets of configuration data for multiple operating modes. One set of configuration data may be selected as desired and loaded from the sets stored in the memory 120.

Figure 7:
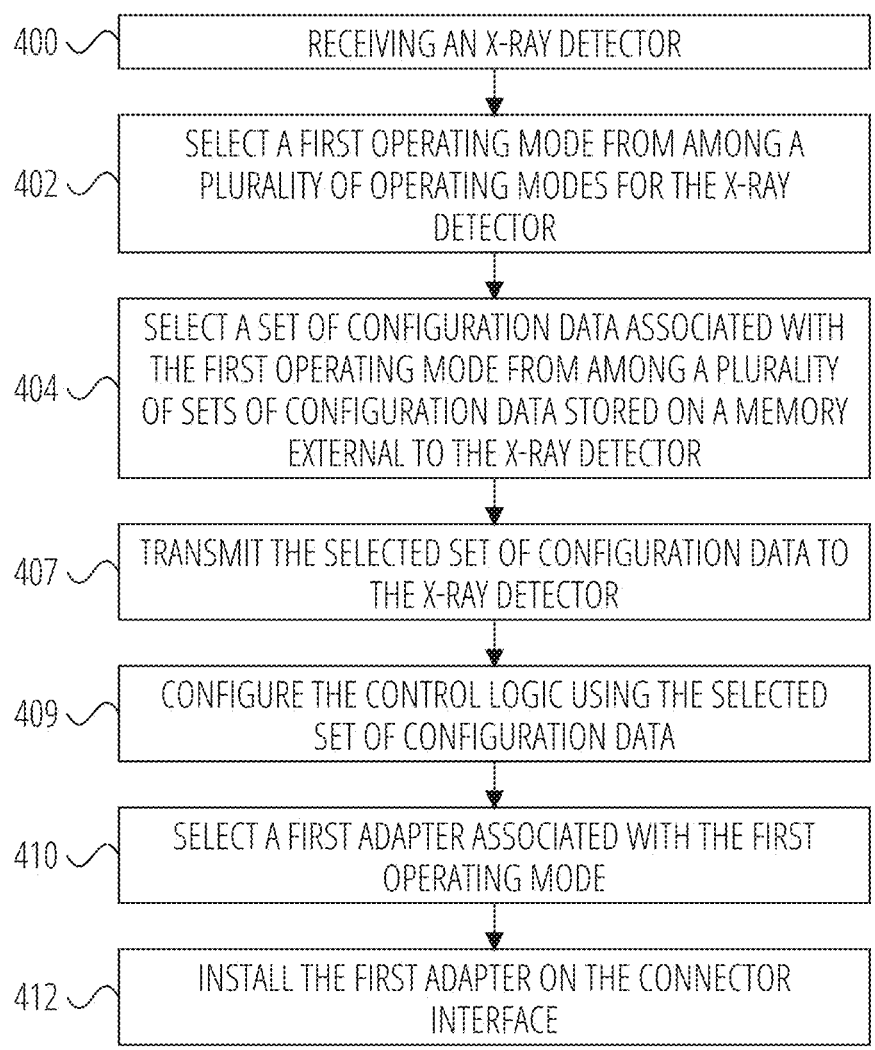
FIG. 7 is a flowchart of configuring an x-ray detector of FIG. 1 according to some embodiments.

FIG. 7 is a flowchart of configuring an x-ray detector of FIG. 1 according to some embodiments. Referring to FIGS. 1 and 7, in some embodiments, the operation may be similar to that of FIGS. 4 and 6. However, in 404, a set of configuration data associated with the first operating mode is selected from among a plurality of sets of confutation data stored on a memory external to the x-ray detector 102. For example, sets of configuration data may be stored on the computer 106, external to the x-ray detector 102.

In 407, the selected set of data is transmitted to the x-ray detector 102. In some embodiments, the set of configuration data is transmitted through the adapter 104. In other embodiments, the set of configuration data may be transmitted through the alternate interface 109. In 409, the control logic 114 is configured using the selected set of configuration data.

Figure 8:
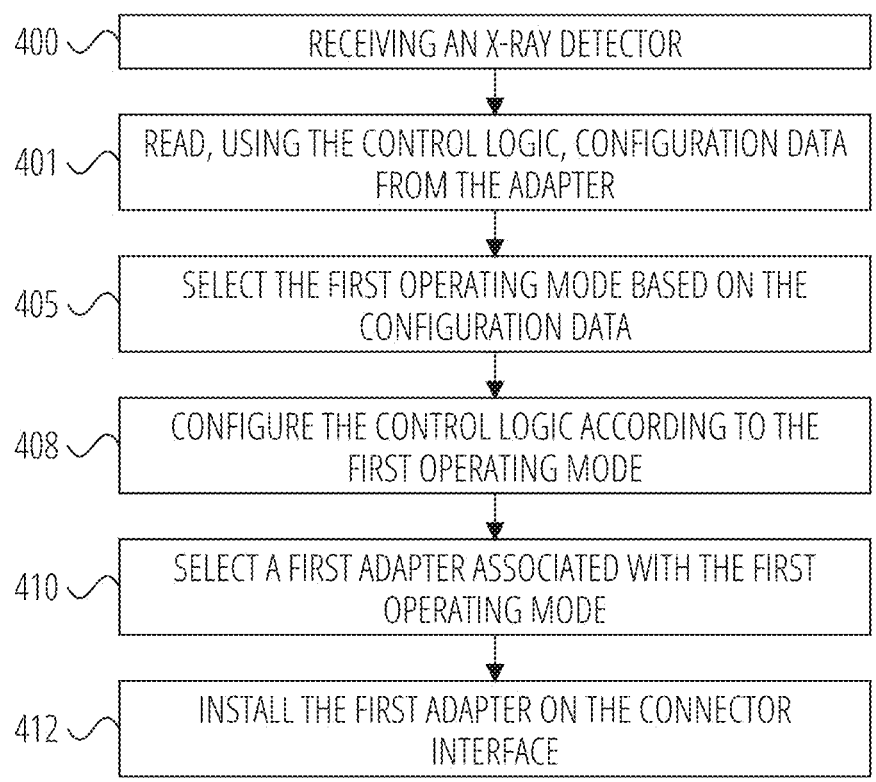
FIG. 8 is a flowchart of configuring an x-ray detector with configuration data based on an adapter according to some embodiments.

FIG. 8 is a flowchart of configuring an x-ray detector with configuration data based on an adapter according to some embodiments. Referring to FIGS. 1 and 8, the operation may be similar to the operation in FIG. 4. In some embodiments, in 401, configuration data is read from the adapter 104 using the control logic 114. In 405, the first operating mode is selected from among the operating modes for the x-ray detector by selecting the first operating mode based on the configuration data.

Figure 9:
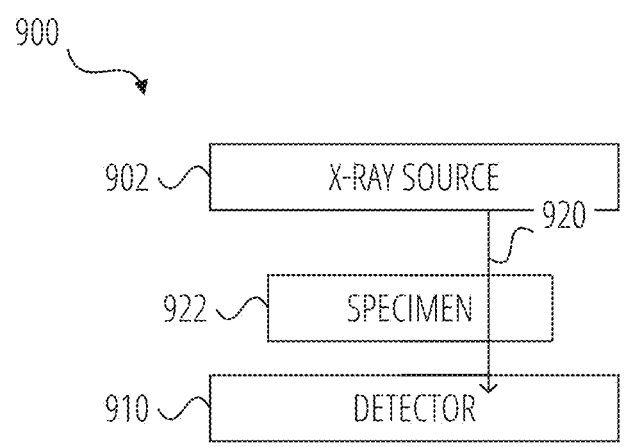
FIG. 9 is a block diagram of an x-ray imaging system according to some embodiments.

FIG. 9 is a block diagram of an x-ray imaging system according to some embodiments. The x-ray imaging system 900 includes an x-ray source 902 and detector 910. The detector 910 may include a modular detector 102' or the like as described above. The x-ray source 902 is disposed relative to the detector 910 such that x-rays 920 may be generated to pass through a specimen 922 and detected by the detector 910. In some embodiments, the detector 910 is part of a medical imaging system. In other embodiments, the x-ray imaging system 900 may include a portable vehicle scanning system as part of a cargo scanning system. The system 900 may be any system that may include an x-ray detector.

An x-ray detector, comprising: a housing 110; an sensory array 112 disposed in the housing 110 and configured to generate image data in response to incident x-rays; a control logic 114 disposed in the housing 110; a connector interface 108 integrated with the housing 110; and an adapter 104 removably couplable to the connector interface 108; wherein: the control logic 114 is configurable to operate in a plurality of operating modes; and for a first operating mode of the operating modes, the control logic 114 is configured to process the image data and/or transmit the image data through the adapter 104 differently than for a second operating mode of the operating modes.

In some embodiments, for the first operating mode, the control logic 114 is configured to transmit the image data using a first protocol different than a second protocol used to transmit the image data for the second operating mode.

In some embodiments, the x-ray detector further comprises a memory 120 configured to store a plurality of sets of configuration data; wherein: each of the operating modes is associated with a corresponding one of the sets of the configuration data.

In some embodiments, the memory 120 is further configured to store an indication of a current operating mode of the operating modes; and the control logic 114 is configured to: select a set of configuration data based on the indication of the current operating mode; and operate in the current operating modes using the selected set of configuration data.

In some embodiments, the control logic 114 is configured to: select one of the operating modes and the associated set of configuration data based on the adapter 104; and operate in the selected one of the operating modes using the associated set of configuration data.

In some embodiments, the first operating mode is a CoaxPress mode; and the second operating mode is an Ethernet mode.

In some embodiments, the connector interface 108 is standardized connector interface 108.

In some embodiments, the control logic 114 and the connector interface 108 are configured to transmit data at a data rate greater than or equal to a greatest data rate among the operating modes.

In some embodiments, the control logic 114 further comprises a processor and a programmable logic device; and the control logic 114 is further configured to perform at least one of: changing software of the processor of the control logic 114 associated with transmission of data through the adapter 104 based on the first operating mode; and changing a configuration of the programmable logic device of the control logic 114 associated with transmission of data through the adapter 104 based on the first operating mode.

A method, comprising: receiving an x-ray detector including: a housing 110; an sensory array 112 disposed in the housing 110 and configured to generate image data in response to incident x-rays; a control logic 114 disposed in the housing 110; and a connector interface 108 integrated with the housing 110; selecting a first operating mode from among a plurality of operating modes for the x-ray detector; configuring the control logic 114 according to the first operating mode; selecting a first adapter 104 associated with the first operating mode; and installing the first adapter 104 on the connector interface 108.

In some embodiments, the method further comprises selecting a second operating mode different from the first operating mode from among the operating modes for the x-ray detector after configuring the control logic 114 according to the first operating mode; and configuring the control logic 114 according to the second operating mode.

In some embodiments, the method further comprises selecting a second adapter 104 different from the first adapter 104 associated with the second operating mode; and installing the second adapter 104 on the connector interface 108.

In some embodiments, configuring the control logic 114 according to the first operating mode comprises: changing software of a processor of the control logic 114 associated with transmission of data through the first adapter 104 based on the first operating mode.

In some embodiments, configuring the control logic 114 according to the first operating mode comprises: changing a configuration of a programmable logic device of the control logic 114 associated with transmission of data through the first adapter 104 based on the first operating mode.

In some embodiments, configuring the control logic 114 according to the first operating mode comprises: selecting a set of configuration data associated with the first operating mode from among a plurality of sets of confutation data stored on a memory 120 within the housing 110 of the x-ray detector; and configuring the control logic 114 using the selected set of configuration data.

In some embodiments, configuring the control logic 114 according to the first operating mode comprises: selecting a set of configuration data associated with the first operating mode from among a plurality of sets of confutation data stored on a memory 120 external to the x-ray detector; transmitting the selected set of configuration data to the x-ray detector; and configuring the control logic 114 using the selected set of configuration data.

In some embodiments, the operating modes includes a second operating mode; the first operating mode is associated with a latency higher than that of the second operating mode; and the first operating mode is associated with a reliability higher than that of the second operating mode.

In some embodiments, configuring the control logic 114 according to the first operating mode comprises reading, using the control logic 114, configuration data from the adapter 104; and selecting the first operating mode from among the operating modes for the x-ray detector comprises selecting the first operating mode based on the configuration data.

An x-ray detector, comprising: means for converting incident x-rays into image data; means for converting a first connector interface into a second connector interface; means for controlling a transmission of the image data through the means for converting the first connector interface into the second connector interface; means for selecting a first operating mode from among a plurality of operating modes for the x-ray detector; and means for configuring means for controlling the transmission of the image data through the means for converting the first connector interface into the second connector interface according to the first operating mode.

Examples of the means for converting incident x-rays into image data include the sensor array 112 or the like. Examples of the means for converting a first connector interface into a second connector interface include the adapter 104 or the like. Examples of the means for controlling a transmission of the image data through the means for converting the first connector interface into the second connector interface include the control logic 114 configured as described above. Examples of the means for selecting a first operating mode from among a plurality of operating modes for the x-ray detector include the control logic 114 configured as described above. Examples of the means for configuring the means for controlling the transmission of the image data through the means for converting the first connector interface into the second connector interface according to the first operating mode include the control logic 114, the memory 120, the computer 106, or the like.

In some embodiments, the x-ray detector further comprises means for storing a plurality of sets of configuration data associated with the operating modes Examples of the means for storing a plurality of sets of configuration data associated with the operating modes include the memory 120, the computer 106, or the like.

Although the structures, devices, methods, and systems have been described in accordance with particular embodiments, one of ordinary skill in the art will readily recognize that many variations to the particular embodiments are possible, and any variations should therefore be considered to be within the spirit and scope disclosed herein. Accordingly, many modifications may be made by one of ordinary skill in the art without departing from the spirit and scope of the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 4 can depend from either of claims 1 and 3, with these separate dependencies yielding two distinct embodiments; claim 5 can depend from any one of claim 1, 3, or 4, with these separate dependencies yielding three distinct embodiments; claim 6 can depend from any one of claim 1, 3, 4, or 5, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112(f). Embodiments of the invention in which an exclusive property or privilege is claimed are defined as follows.

The invention claimed is:
1. An x-ray detector, comprising:
a housing;
a sensor array disposed in the housing and configured to generate image data in response to incident x-rays;
a control logic disposed in the housing;
a connector interface integrated with the housing; and
an adapter removably couplable to the connector interface;
wherein:
the control logic is configurable to operate in a plurality of operating modes; and
for a first operating mode of the operating modes, the control logic is configured to process the image data and/or transmit the image data through the adapter differently than for a second operating mode of the operating modes; and
for the first operating mode, the control logic is configured to transmit the image data using a first protocol different than a second protocol used to transmit the image data for the second operating mode.

2. The x-ray detector of claim 1, further comprising:
a memory configured to store a plurality of sets of configuration data;
wherein:
each of the operating modes is associated with a corresponding one of the sets of the configuration data.

3. The x-ray detector of claim 2, wherein:
the memory is further configured to store an indication of a current operating mode of the operating modes; and
the control logic is configured to:
select a set of configuration data based on the indication of the current operating mode; and
operate in the current operating mode using the selected set of configuration data.

4. The x-ray detector of claim 2, wherein the control logic is configured to:
select one of the operating modes and the associated set of configuration data based on the adapter; and
operate in the selected one of the operating modes using the associated set of configuration data.

5. The x-ray detector of claim 1, wherein:
the first operating mode is a CoaxPress mode; and
the second operating mode is an Ethernet mode.

6. The x-ray detector of claim 1, wherein:
the connector interface is standardized connector interface.

7. The x-ray detector of claim 1, wherein:
the control logic and the connector interface are configured to transmit data at a data rate greater than or equal to a greatest data rate among the operating modes.

8. The x-ray detector of claim 1, wherein:
the control logic further comprises a processor and a programmable logic device; and
the control logic is further configured to perform at least one of:
  changing software of the processor of the control logic associated with transmission of data through the adapter based on the first operating mode; and
  changing a configuration of the programmable logic device of the control logic associated with transmission of data through the adapter based on the first operating mode.

9. A method, comprising:
receiving an x-ray detector including:
  a housing;
  a sensor array disposed in the housing and configured to generate image data in response to incident x-rays;
  a control logic disposed in the housing; and
  a connector interface integrated with the housing;
selecting a first operating mode from among a plurality of operating modes for the x-ray detector;
configuring the control logic according to the first operating mode;
selecting a first adapter associated with the first operating mode; and
installing the first adapter on the connector interface.

10. The method of claim 9, further comprising:
selecting a second operating mode different from the first operating mode from among the operating modes for the x-ray detector after configuring the control logic according to the first operating mode; and
configuring the control logic according to the second operating mode.

11. The method of claim 10, further comprising: selecting a second adapter different from the first adapter associated with the second operating mode; and installing the second adapter on the connector interface.

12. The method of claim 9, wherein configuring the control logic according to the first operating mode comprises:
changing software of a processor of the control logic associated with transmission of data through the first adapter based on the first operating mode.

13. The method of claim 9, wherein configuring the control logic according to the first operating mode comprises:
changing a configuration of a programmable logic device of the control logic associated with transmission of data through the first adapter based on the first operating mode.

14. The method of claim 9, wherein configuring the control logic according to the first operating mode comprises:
selecting a set of configuration data associated with the first operating mode from among a plurality of sets of configuration data stored on a memory within the housing of the x-ray detector; and
configuring the control logic using the selected set of configuration data.

15. The method of claim 9, wherein configuring the control logic according to the first operating mode comprises:
selecting a set of configuration data associated with the first operating mode from among a plurality of sets of configuration data stored on a memory external to the x-ray detector;
transmitting the selected set of configuration data to the x-ray detector; and
configuring the control logic using the selected set of configuration data.

16. The method of claim 9, wherein:
the operating modes includes a second operating mode;
the first operating mode is associated with a latency higher than that of the second operating mode; and
the first operating mode is associated with a reliability higher than that of the second operating mode.

17. The method of claim 9, wherein:
configuring the control logic according to the first operating mode comprises reading, using the control logic, configuration data from the adapter; and
selecting the first operating mode from among the operating modes for the x-ray detector comprises selecting the first operating mode based on the configuration data.

18. An x-ray detector, comprising:
means for converting incident x-rays into image data;
means for converting a first connector interface into a second connector interface;
means for controlling a transmission of the image data through the means for converting the first connector interface into the second connector interface;
means for selecting a first operating mode from among a plurality of operating modes for the x-ray detector; and
means for configuring the means for controlling the transmission of the image data through the means for converting the first connector interface into the second connector interface according to the first operating mode;
wherein for the first operating mode, the means for controlling the transmission of the image data through the means for converting the first connector interface into the second connector interface is configured to transmit the image data using a first protocol different than a second protocol used to transmit the image data for a second operating mode of the operating modes.

19. The x-ray detector of claim 18, further comprising:
means for storing a plurality of sets of configuration data associated with the operating modes.

* * * * *